United States Patent [19]

Blass

[11] Patent Number: 5,800,823
[45] Date of Patent: Sep. 1, 1998

[54] ELONGATE PTFE ELEMENTS AND ARTICLES MADE THEREOF

[75] Inventor: Jacob Moses Blass, London, United Kingdom

[73] Assignee: Caredent Limited, London, England

[21] Appl. No.: 772,283

[22] Filed: Dec. 20, 1996

[30] Foreign Application Priority Data

Dec. 27, 1995 [GB] United Kingdom ............ 9526551

[51] Int. Cl.[6] .................................................. A61K 9/00
[52] U.S. Cl. .................... 424/400; 424/435; 424/49; 424/52; 424/443
[58] Field of Search .......................... 424/400, 435, 424/443; 132/321

[56] References Cited

U.S. PATENT DOCUMENTS

| | | |
|---|---|---|
| 3,943,949 | 3/1976 | Ashton et al. . |
| 4,482,516 | 11/1984 | Bowman et al. ............ 264/127 |
| 5,209,251 | 5/1993 | Curtis et al. ............... 132/321 |
| 5,413,127 | 5/1995 | Hill ............................ 132/321 |

FOREIGN PATENT DOCUMENTS

| | | |
|---|---|---|
| 3354666A2 | 10/1989 | European Pat. Off. . |
| 0358363 | 3/1990 | European Pat. Off. . |
| 2 128133 | 4/1984 | United Kingdom . |
| 92/10978 | 7/1992 | WIPO . |
| 96/10478 | 4/1996 | WIPO . |

*Primary Examiner*—Thurman K. Page
*Assistant Examiner*—William E. Benston, Jr.
*Attorney, Agent, or Firm*—Larson & Taylor

[57] ABSTRACT

An elongate PTFE (polytetrafluoroethylene) element is formed, having a PTFE matrix and containing a water soluble additive material in the form of solid particles distributed within the matrix. The PTFE elements may be twisted or untwisted tape, and a plurality of elements may be twisted together to form a fiber. Such elements or fibers may be formed into articles for use in dentistry, such as dental floss, or into medical sutures, woven filter mesh and other non-dental articles.

14 Claims, No Drawings

ELONGATE PTFE ELEMENTS AND ARTICLES MADE THEREOF

FIELD OF THE INVENTION

This invention relates to elongate PTFE elements and articles made thereof, particularly but not exclusively dental articles, such as dental floss, astyptic material for use in contact with the teeth and periodontal dressings. In the articles the tensile strength of the article is provided at least partly by at least one elongate integral element of PTFE (polytetrafluoroethylene). This element of PTFE is typically a twisted or untwisted tape, and a plurality of the elongate elements may be twisted together to form a fiber. Such elements or fibers may be formed into articles for uses other than dentistry, such as medical sutures, wound dressings and woven filter mesh. By the expression "integral element" it is meant that the element is a unitary body of PTFE. The invention also relates to a method of making the PTFE element.

BACKGROUND OF THE INVENTION AND PRIOR ART STATEMENT

In recent years, PTFE dental floss has been successfully marketed. Published patent documents include EP-A-335466 and WO92/10978, which describe dental flosses made of sintered PTFE which are coated with wax. WO 96/10478 describes manufacture of a new form of PTFE which is suitable for use as a dental floss, either coated with wax or in uncoated form, by reason of its surface properties.

EP335466 and WO92/10978 both also propose that additives, such as dentifrices and components having a pharmaceutical or other beneficial effect when released in the mouth, are incorporated in the dental floss. This might be done either in the wax or as a substrate coating on the PTFE before the wax is applied. In EP335466 it is also suggested that the additive might be incorporated into the floss filament prior to coating by immersion of the floss. Another proposal is that polishing agents, which are by nature insoluble, might be mixed with the PTFE during formation.

In order that an additive shall be released in the mouth, on contact of the floss or other material with liquid in the mouth, the additive must be water-soluble. The water-soluble additive should desirably be incorporated in to the floss in a manner such that it releases rapidly and in sufficient quantity in use, but an excessive quantity cannot be incorporated into the floss because of the risk of release of an excessive amount on prolonged contact. Therefore a high proportion, e.g. over 50% of the additive should be released within a short time period.

SUMMARY OF THE INVENTION

The present inventor has now found that surprisingly, a water-soluble additive, intended to be released in the mouth, can be incorporated in a suitable manner in the PTFE by mixing it in particulate form into a PTFE, prior to the formation of the PTFE into the PTFE element. This finding also has uses in other fields, for example sutures, wound dressings and filter meshes, where release of a water-soluble additive is required.

According to the invention in one aspect, there is provided an elongate integral element of PTFE having a PTFE matrix and containing a water-soluble additive material in the form of solid particles distributed within said matrix. The element is preferably tape-shaped. The element may be twisted. There is also provided a fiber composed of a plurality of such elongate elements twisted together.

According to the invention in another aspect there is provided an elongate dental article which is a preferably selected from a dental floss, an astyptic material for use in contact with the teeth and a periodontal dressing, comprising at least one elongate integral element of PTFE of the invention as defined above.

In another aspect, the invention provides a method of forming an elongate integral PTFE element, comprising the steps of preparing a mixture of a PTFE material and a particulate water-soluble additive material, and extruding said mixture and heat treating the extrudate, optionally with lengthwise extension thereof, to prepare an elongate PTFE element having a PTFE matrix and containing said water-soluble additive material in the form of solid particles distributed within said matrix.

The present inventor has surprisingly found that solid particles of water-soluble material incorporated in this manner within the PTFE matrix are released rapidly and in substantial quantities, e.g. more than 50%, in a short time, e.g. 3 minutes, when in contact with aqueous fluid. This is contrary to the expectation that the PTFE matrix is likely to prevent the rapid solution of the additive out of the matrix, because of the poor wettability of PTFE by water.

Conventionally, elongate PTFE elements are made by mixing a PTFE powder with lubricant and optionally other fillers, extruding the mixture to produce an unsintered tape or sheet, calendering the tape or sheet, removing the lubricant by heat treatment and then subjecting the tape or sheet to a further heat-treatment, which usually involves at least partial sintering of the PTFE to produce a material whose strength can be selected by appropriate selection of the heat treatment process parameters. The second heat treatment may include uniaxial or biaxial stretching, and in particular may include expansion i.e. density reduction, which results in a more porous product. Such processes are well known. Improvements in these processes are published in WO 96/10478 referred to above, and the contents of that publication are herein incorporated by reference. In the present invention, any of these known processes may be employed, provided that the water-soluble additive is incorporated as a particulate material, i.e. a powder, in the PTFE powder, prior to the extrusion step.

The particulate additive may be incorporated in the PTFE powder in a mixer, such as a cone mixer or a blade mixer, and the temperature should preferably be held below 20° C. in the mixer to avoid caking and fibrillation of the PTFE.

In an alternative process within the invention, the particulate water-soluble material may be added to a dispersion of PTFE powder, which is thereafter dried to provide an intimate mixture of PTFE powder and the water-soluble component. This mixture is then subjected to the further processing (extrusion, sintering) described above. Prior to mixing with lubricant for extrusion, the mixture may be sieved or refined to provide a suitable particle size, as necessary. Suitable dispersions are available from PTFE manufacturers.

Any suitable water-soluble material may be included in the PTFE, in accordance with the invention. Examples of such materials are soluble fluorides such as sodium fluoride, potassium fluoride, ammonium fluoride, soluble plaque control agents and tartar control agents, soluble antibacterial agents, soluble anti-inflammatory agents, soluble anti-fungal agents, vitamins such as vitamin C, surfactants and flavouring materials. Particularly preferred materials are, in dental articles such as dental floss, soluble fluoride, chlorhexidine acetate, chlorhexidine gluconate, zinc citrate, cetylpyridinium chloride, sodium pyrophosphate and potassium pyrophosphate, and in an astyptic element aluminium chloride and ferric chloride. Other materials which may be included in the PTFE are enzymes which have a beneficial effect in the mouth, such as dextranase, bromelain and papain.

An astyptic article is preferably formed of a plurality of PTFE elements in accordance with the invention.

In the case of a soluble fluoride, such as NaF, KF or NH$_3$F, the amount of fluoride incorporated by weight is preferably in the range of 0.01 to 3% of the weight of PTFE, more preferably 0.1 to 1%. The preferred amount for the additive chlorhexidine is in the range 0.1–2%, more preferably 0.25–1%.

The average particle size of the particulate additive water-soluble material included in the PTFE powder is preferably in the range of 0.1 μm to 100 μm. The narrower range 1 to 100 μm, preferably 1 to 20 μm is suitable, but it is believed that small particles in the size range 0.2 to 1 μm may also be employed. In subsequent processing into the elongate PTFE element, the particulate additive material will in general remain unchanged, although in some cases it may undergo some size change.

The particle size of the PTFE is any suitable one, but is preferably in the range 200–800 μm, more preferably 400–600 μm.

It is of course necessary that the incorporated water-soluble additive is resistant to the heat-treatment which follows its incorporation. This heat-treatment may involve a temperature as high as 325° C., the sintering temperature of PTFE.

EMBODIMENTS OF THE INVENTION

In one example of the invention, sodium fluoride powder (anhydrous) is incorporated in powder PTFE in an amount of 0.3% by weight. The powder size of the NaF is such that 97% passes a 200 USS sieve (73 μm aperture size). The PTFE and NaF particles are thoroughly mixed in a tumble mixer. This mixture is subjected to conventional extrusion (with a suitable lubricant) into a tape. After calendaring and removal of the lubricant, the tape is slit into a plurality of narrow elements, and these elements are subjected to a heat treatment involving elongation and sintering, with expansion, to provide a dental floss material, as described in WO 96/10478. The dental floss was used without wax coating. To test the release of the fluoride ion, the floss was immersed in water at 37° C. for 3 minutes. In this time, the quantity of NaF released from the floss was 0.184% by weight relative to the weight of the dental floss, i.e. a release of more than 50% of the total NaF. This amount of release, in this time period, is very much more than is obtained by mixing sodium fluoride in a wax which is applied to the PTFE element.

In a dental floss of the invention, preferably the tensile strength of the PTFE is at least 100 MPa, e.g. in the range 200–600 MPa. Preferably the PTFE is a monofilament ribbon, and preferably the width of the ribbon is in the range 0.5–4 mm, more preferably 1–3 mm, most preferably 1.2–2.4 mm. The thickness is preferably in the range 20 to 120 μm, more preferably 20–60 μm and most preferably 30–50 μm. The dental floss is unwaxed.

An astyptic material of the invention preferably is an elongate material of 300 to 3000 decitex.

As mentioned, the invention also provides a fiber formed of a plurality of elongate integral PTFE elements of the invention. Such a fiber may have a variety of uses in the medical and other fields, such as in a suture, a woven wound dressing or a woven filter mesh. The fiber preferably consists of 2 to 50, more preferably 2 to 5 integral PTFE elements of the invention twisted together in parallel. A fiber of three such elements twisted together may have the following specification:

350–500 dtex, e.g. 400 dtex elongation at break 15–25% tenacity 25–35 cN/tex breaking force 10–20N, e.g. 17N shrinkage (220° C.) less than 3%

As usual, the term PTFE in this application includes a range of fluoropolymers.

I claim:

1. A filament comprising the elongate integral PTFE element which provides the tensile strength of the filament, said PTFE element comprising an extruded matrix of PTFE and containing a water-soluble additive material in the form of solid particles of average particle size in the range 0.1 to 100 μm, distributed in said matrix.

2. A dental article comprising at least one filament comprising an elongate integral PTFE element which provides the tensile strength of the filament, said PTFE element comprising an extruded matrix of PTFE and containing a water-soluble additive material in the form of solid particles of average particle size in the range 0.1 to 100 μm distributed in said matrix.

3. A dental article according to claim 2, which is one of a dental floss, an astyptic material for use in contact with the teeth, and a periodontal dressing.

4. A dental article according to 2, wherein said water-soluble additive material is selected from soluble fluorides, soluble plaque control agents, soluble tartar control agents, soluble anti-bacterial agents, soluble anti-inflammatory agents, soluble anti-fungal agents, soluble vitamins, surfactants, and soluble flavouring materials.

5. A dental article according to claim 2, wherein the average particle size of said water-soluble additive material is in the range 1 to 100 μm.

6. A method of forming a filament in the form of an elongate integral PTFE element which provides the tensile strength of the filament, comprising the steps of preparing a mixture of a PTFE material and a particulate water-soluble additive material, extruding said mixture into an elongate extrudate and heat treating the extrudate, optionally with lengthwise extension thereof, to prepare said elongate integral PTFE element having a PTFE matrix providing said tensile strength and containing said water-soluble additive material in the form of solid particles distributed within said matrix.

7. A method of making a dental article which comprises a filament in the form of an elongate integral PTFE element which provides the tensile strength of the filament, comprising the steps of preparing a mixture of a PTFE material and a particulate water-soluble additive material, extruding said mixture into an elongate extrudate and heat treating the extrudate, optionally with lengthwise extension thereof, to prepare said elongate integral PTFE element having a PTFE matrix and containing said water-soluble additive material in the form of solid particles distributed within said matrix.

8. A fiber comprising a plurality of filaments twisted together, each of said filaments being an elongate integral PTFE element which provides the tensile strength of the filament, said PTFE element comprising an extruded matrix of PTFE and containing a water-soluble additive material in the form of solid particles of average particle size in the range 0.1 to 100 μm distributed in said matrix.

9. A fiber according to claim 8 wherein in each said filament said PTFE matrix is at least partly sintered.

10. A filament according to claim 1, wherein said PTFE matrix is at least partly sintered.

11. A method according to claim 6, wherein during said heat-treating step said PTFE material is at least partly sintered.

12. A method according to claim 6, wherein said particles have an average particle size in the range 0.1 to 100 μm.

13. A method according to claim 7, wherein during said heat-treating step said PTFE material is at least partly sintered.

14. A method according to claim 7, wherein said solid particles have an average particle size in the range 0.1 to 100 μm.

* * * * *